US007342092B2

(12) United States Patent
Sugiyama

(10) Patent No.: US 7,342,092 B2
(45) Date of Patent: Mar. 11, 2008

(54) CANCER ANTIGEN PEPTIDE FORMULATIONS

(75) Inventor: Haruo Sugiyama, Minoo (JP)

(73) Assignee: International Institute of Cancer Immunology, Inc., Suita-shi (JP)

( * ) Notice: Subject to any disclaimer, the term of this patent is extended or adjusted under 35 U.S.C. 154(b) by 300 days.

(21) Appl. No.: 10/527,692

(22) PCT Filed: Sep. 12, 2003

(86) PCT No.: PCT/JP03/11675

§ 371 (c)(1),
(2), (4) Date: Mar. 11, 2005

(87) PCT Pub. No.: WO2004/024175

PCT Pub. Date: Mar. 25, 2004

(65) Prior Publication Data

US 2007/0036808 A1    Feb. 15, 2007

(30) Foreign Application Priority Data

Sep. 12, 2002    (JP)    ............................ 2002-266876

(51) Int. Cl.
*A61K 38/00*    (2006.01)
*C07K 5/00*    (2006.01)
*C07K 7/00*    (2006.01)
*C07K 16/00*    (2006.01)
*C07K 17/00*    (2006.01)

(52) U.S. Cl. .......................................... 530/324; 514/2
(58) Field of Classification Search ..................... None
See application file for complete search history.

(56) References Cited

U.S. PATENT DOCUMENTS

| 6,034,235 | A | 3/2000 | Sugiyama et al. | |
|---|---|---|---|---|
| 6,277,832 | B1 | 8/2001 | Sugiyama et al. | |
| 2003/0082194 | A1* | 5/2003 | Gaiger et al. | 424/184.1 |
| 2003/0092656 | A1 | 5/2003 | Sugiyama | |
| 2004/0097703 | A1 | 5/2004 | Sugiyama | |
| 2004/0247609 | A1 | 12/2004 | Sugiyama | |
| 2005/0002951 | A1 | 1/2005 | Sugiyama et al. | |
| 2005/0266014 | A1 | 12/2005 | Sugiyama et al. | |

FOREIGN PATENT DOCUMENTS

| EP | 1 103 564 A1 | 5/2001 |
|---|---|---|
| EP | 1 371 664 A1 | 12/2003 |
| WO | WO-00/06602 A1 | 2/2000 |
| WO | WO-00/18795 A | 4/2000 |
| WO | WO-00/26249 A1 | 5/2000 |
| WO | WO-02/079253 A1 | 10/2002 |

OTHER PUBLICATIONS

Cancer Prevention Overview (PDQ), Health Professional Version (on-line publication, www.cancer.gov/cancertopics/pdq/prevention/overview/healthProfessional/. Natiional Cancer Institute, U.S. National Institutes of Health. Last modified Mar. 2, 2007. pp. 1-5.*
NCI Drug Dictionary. HLA-A1, A2, B35-restricted survivin peptides/Montanide ISA-51 vaccine. http://www.cancer.gov/Templates/drugdictionary.aspx?cdrid=433196&page=1&print=1.*
U.S. Appl. No. 10/527,692, filed Mar. 11, 2005, Sugiyama.
U.S. Appl. No. 10/562,486, filed Dec. 27, 2005, Sugiyama.
U.S. Appl. No. 11/322,245, filed Jan. 3, 2006, Sugiyama, et al.
U.S. Appl. No. 09/744,815, filed Jan. 30, 2001, Sugiyama, et al.
U.S. Appl. No. 10/517,600, filed Dec. 13, 2004, Sugiyama, et al.
U.S. Appl. No. 10/528,360, filed Mar. 18, 2005, Sugiyama, et al.
U.S. Appl. No. 11/196,452, filed Aug. 4, 2005, Sugiyama, et al.
U.S. Appl. No. 10/541,821, filed Jul. 11, 2005, Sugiyama, et al.
Rosenberg, Immunity, vol. 10, pp. 281-287 (Mar. 1999).
Bakker et al., The Journal of Experimental Medicine, vol. 179, pp. 1005-1009 (Mar. 1994).
Kawakami et al., Proc. Natl. Acad. Sci. USA, vol. 91, pp. 3515-3519 (Apr. 1994).
Brichard et al., J. Exp. Med., vol. 178, pp. 489-495 (Aug. 1993).
Fisk et al., J. Exp. Med., vol. 181, pp. 2109-2117 (Jun. 1995).
Tsang et al., Journal of the National Cancer Institute, vol. 87, No. 13, pp. 982-990 (Jul. 5, 1995).
Correale et al., Journal of the National Cancer Institute, vol. 89, No. 4, pp. 293-300 (Feb. 19, 1997).
Melief et al., Cur. Opin. Immunol, vol. 5, pp. 709-713 (1993).
Pardoll, Cur. Opin. Immunol, vol. 5, pp. 719-725 (1993).
Nanda et al., Cell, vol. 82, pp. 13-17 (Jul. 14, 1995).
Melief et al., Immunological Reviews, No. 146, pp. 167-177 (1995).
Gessler et al., Nature, vol. 343, pp. 774-778 (Feb. 22, 1990).
Call et al., Cell, vol. 60, pp. 509-520 (Feb. 9, 1990).
Oka et al., The Journal of Immunology, vol. 164, pp. 1873-1880 (2000).
Tsuboi et al., Journal of Clinical Immunology, vol. 20, No. 3, pp. 195-202 (2000).

* cited by examiner

*Primary Examiner*—Cecilia J. Tsang
*Assistant Examiner*—Maury Audet
(74) *Attorney, Agent, or Firm*—Oblon, Spivak, McClelland, Maier & Neustadt, P.C.

(57) ABSTRACT

Cancer antigen peptides derived from WT1 which have an in vivo efficacy, particularly a clinical usefulness, and cancer vaccines as dosage forms suitable for said cancer antigen peptides, are provided.

The invention relates to water-in-oil emulsions which comprise as an effective ingredient either one or both of peptides selected from the group consisting of a peptide having an amino acid sequence of Cys Met Thr Trp Asn Gln Met Asn Leu (SEQ ID NO: 2), and a peptide having an amino acid sequence of Cys Tyr Thr Trp Asn Gln Met Asn Leu (SEQ ID NO: 3), as well as processes for preparation of said emulsion.

7 Claims, 2 Drawing Sheets

CANCER ANTIGEN PEPTIDE FORMULATIONS

TECHNICAL FIELD

The present invention relates to formulations comprising an HLA-A24-restricted cancer antigen peptide. Specifically, it relates to emulsion formulations used as a cancer vaccine for treatment of various cancers, and kits for preparation of the formulations.

BACKGROUND ART

Cellular immunities, particularly cytotoxic T cells (referred to as CTLs hereinafter), play an important role in the elimination of cancer cells or virus-infected cells from a living body. CTLs recognize a complex formed between an antigen peptide derived from a cancer antigen protein on a cancer cell (cancer antigen peptide) and an MHC (Major Histocompatibility Complex) class I antigen (referred to as an HLA antigen in the case of human), and thereby attack and injure cancer cells.

Representative examples of cancer antigen proteins are listed in Tables described in *Immunity*, vol. 10: 281, 1999. Specific examples include melanosomal antigens such as a melanocytic tissue-specific protein, gp100 (*J. Exp. Med.*, 179:1005, 1994), MART-1 (*Proc. Natl. Acad. Sci. USA*, 91:3515, 1994), and tyrosinase (*J. Exp. Med.*, 178:489, 1993); as well as cancer markers such as HER2-neu (*J. Exp. Med.*, 181:2109, 1995), CEA (*J. Natl. Cancer Inst.*, 87:982, 1995) and PSA (*J. Natl. Cancer Inst.*, 89:293, 1997) as cancer antigen proteins other than those from melanomas. Cancer antigen peptides are peptides consisting of about 8 to 11 amino acid residues, which are generated through the processing of cancer antigen proteins with intracellular proteases (*Cur. Opin, Immunol.*, 5:709, 1993; *Cur. Opin, Immunol.*, 5: 719, 1993; *Cell*, 82: 13, 1995; *Immunol. Rev.*, 146: 167, 1995). The cancer antigen peptides thus generated bind to MHC class I antigens (HLA antigens) to form complexes, and then the complexes are presented on cellular surfaces, and recognized by CTLs as described above. In development of medical products for cancer immunotherapy (cancer vaccines) based on cancer cells disruption by CTLs, it therefore is very important to identify a cancer antigen peptide from the cancer antigen protein, which can effectively induce CTLs.

Lots of subtypes exist in MHC class I antigen molecules, and the amino acid sequence of an antigen peptide that can bind to the respective subtype obeys a certain rule (binding motif corresponding to a type of MHC antigen molecules. Regarding the binding motif for HLA-A2, for example, the amino acid at position 2 is leucine, methionine, or isoleucine, and the amino acid at position 9 is valine, leucine, or isoleucine. Regarding the binding motif for HLA-A24, the amino acid at position 2 is tyrosine, phenylalanine, methionine, or tryptophan, and the amino acid at position 9 is phenylalanine, leucine, isoleucine, tryptophan, or methionine. Recently, any peptide sequence expected to be capable of binding to HLA antigens including the motifs as shown above may be searched on databases (for example, BIMAS software; http://bimas.dcrt.nih.gov/molbio/hla_bind/). Accordingly, in order to identify a cancer antigen peptide that can induce CTLs from the cancer antigen protein, peptide regions consisting of about 8 to 11 amino acid residues that match the binding motif or the peptide sequence expected for an intended HLA type are first identified from the amino acid sequence of the cancer antigen protein.

However, a peptide that has been identified based on the binding motif or the expected peptide sequence does not necessarily have an activity to induce CTLs. Since a cancer antigen peptide is generated through the intracellular processing of a cancer antigen protein, a peptide not having been generated through the processing cannot be an antigen peptide. Furthermore, since many cancer antigen proteins exist originally in a living body, CTLs may be tolerant to such cancer antigens even if a peptide having the binding motif or the expected binding sequence is intracellularly generated as a cancer antigen peptide. Those show that, in order to identify a cancer antigen peptide having an activity to induce CTLs, a prediction merely based on the binding motif or the peptide sequence expected for an intended HLA type is insufficient, and an in vivo evaluation for an activity to induce CTLs should be important.

A Wilms cancer suppressor gene WT1 (WT1 gene) was isolated from chromosome 11p13 as one of the causative genes of Wilms cancers based on the analysis of the WAGR syndrome that was complicated by Wilms cancers, aniridia, urogenital anomaly, mental retardation, etc. (*Nature*, 343: 774, 1990). The genomic DNA of WT1 is about 50 Kb, and is composed of ten exons, of which the cDNA is about 3 kb. The amino acid sequence deduced from the cDNA is as shown in SEQ ID NO: 1 (*Cell.*, 60:509, 1990). The WT1 gene has been suggested to promote the growth of leukemia cells from the facts that the WT1 gene is highly expressed in human leukemia, and that the leukemia cells are suppressed in their cellular growth by the treatment with WT1 antisense oligomers (Japanese Patent Publication (Kokai) No. 104627/1997). Then, the WT1 gene has been demonstrated to be a new cancer antigen protein of leukemia and solid cancers (*J. Immunol.*, 164: 1873-80, 2000, *J. Clin. Immunol.*, 20, 195-202, 2000) from the fact that the WT1 gene is also highly expressed in solid cancers such as gastric cancer, colon cancer, lung cancer, breast cancer, embryonal cancer, skin cancer, bladder cancer, prostate cancer, uterine cancer, cervical cancer, and ovarian cancer (Japanese Patent Publication (Kokai) No. 104627/1997, Japanese Patent Publication (Kokai) No. 35484/1999). Cancer immunotherapy (cancer vaccines) can be preferably applied to as many as possible of cancer patients, and therefore it is important to identify cancer antigen peptides from WT1, which is highly expressed in many kinds of cancers, and to develop cancer vaccines based on those cancer antigen peptides. In this context, WO00/06602 and WO00/18795 describe natural-type cancer antigen peptides composed of a portion of the WT1 protein, but those cancer antigen peptides have not been yet examined for their in vivo efficacy.

DISCLOSURE OF THE INVENTION

The present invention aims to provide cancer antigen peptides derived from WT1, which have an in vivo efficacy, particularly a clinical usefulness, and cancer vaccines as dosage forms suitable for said cancer antigen peptides.

The inventor of the present application conducted the clinical study of patients who had given informed consent with the approval of the Ethical Review Board of the Faculty of Medicine, Osaka University, and found that the administration of some cancer antigen peptides in a particular dosage form to cancer patients efficiently ameliorates their pathological conditions, thus accomplishing the present invention.

Thus, the present invention relates to:

(1) a water-in-oil emulsion which comprises as an effective ingredient either one or both of peptides selected from the group consisting of a peptide having an amino acid sequence of Cys Met Thr Trp Asn Gln Met Asn Leu (SEQ ID NO: 2), and a peptide having an amino acid sequence of Cys Tyr Thr Trp Asn Gln Met Asn Leu (SEQ ID NO: 3); particularly the emulsion according to the invention wherein the emulsion is in a dosage unit form that comprises 0.1 to 100 mg of the peptide; preferably the emulsion according to the invention wherein the emulsion is to be used as a cancer vaccine:

(2) a process for preparation of the water-in-oil emulsion according to the invention, which comprises mixing a preparation comprising either one or both of peptides selected from the group consisting of a peptide having an amino acid sequence of SEQ ID NO: 2, and a peptide having an amino acid sequence of SEQ ID NO: 3, together with an emulsifier and an oil: and (3) a kit for preparation of the water-in-oil emulsion according to the invention, which includes a container comprising either one or both of peptides selected from the group consisting of a peptide having an amino acid sequence of SEQ ID NO: 2, and a peptide having an amino acid sequence of SEQ ID NO: 3, and a container comprising an emulsifier and an oil; preferably the kit according to the invention wherein the kit is to be used in the preparation of the emulsion just before use.

Figure 1:
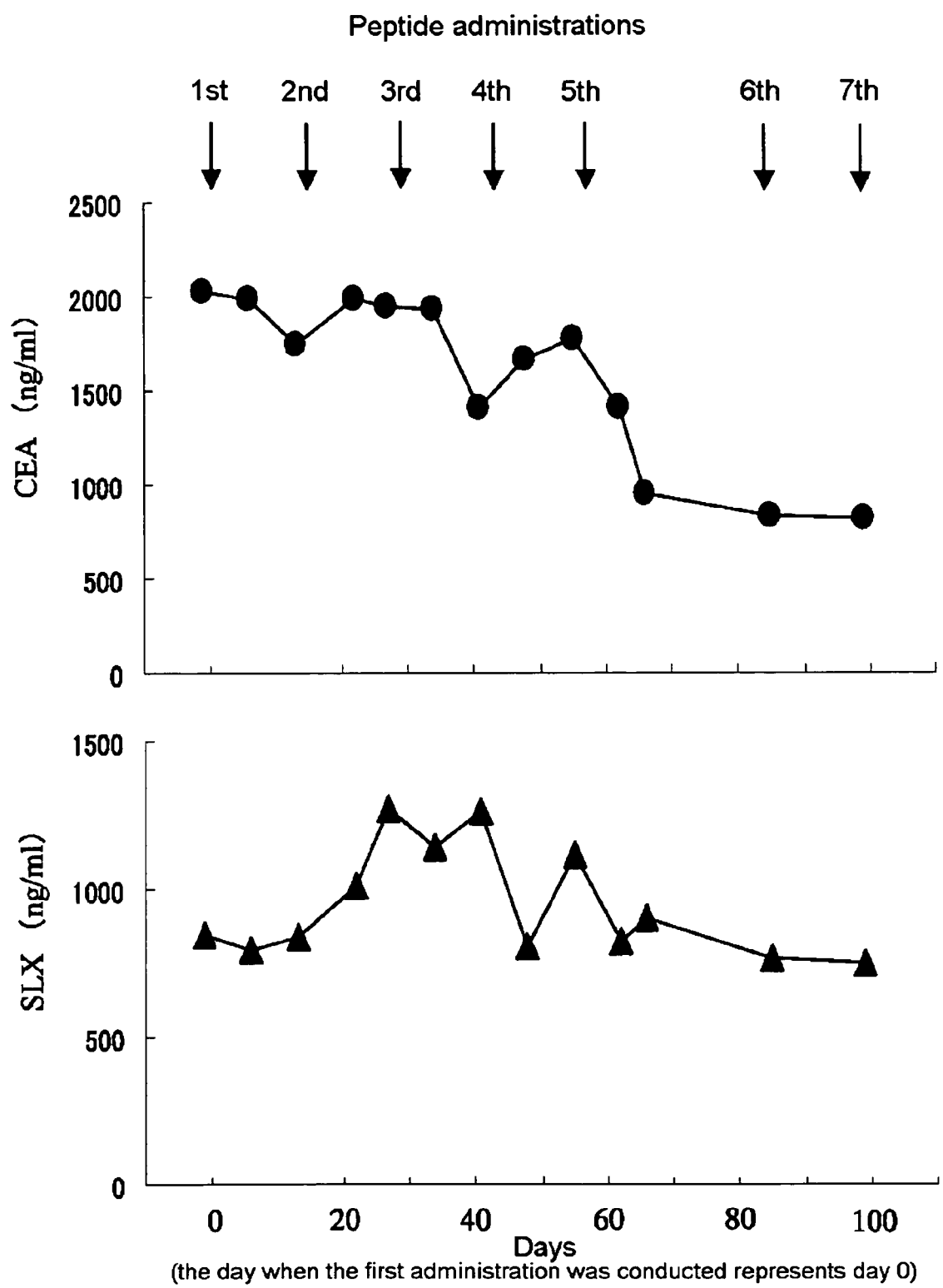
FIG. 1 is graphs showing the change in tumor marker levels in the lung cancer patient (female) before and after the administration of wild type WT1 peptide (SEQ ID NO: 2).

BEST MODE FOR CARRYING OUT THE INVENTION (1) Effective Ingredient

A peptide having an amino acid sequence of SEQ ID NO: 2 or SEQ ID NO: 3 comprised as an effective ingredient in a water-in-oil emulsion of the present invention is derived from human WT1 (*Cell.*, 60:509, 1990, NCBI database Accession No. XP_034418, SEQ ID NO: 1). Specifically, a peptide having an amino acid sequence of SEQ ID NO: 2 is a partial peptide spanning from positions 235 to 243 in human WT1 (WO00/06602), whereas a peptide having an amino acid sequence of SEQ ID NO: 3 is an altered type peptide wherein Met at position 236 in the spanning region of positions 235 to 243 is altered into Tyr (WO02/079253 (International publication date: Oct. 10, 2002)).

The inventor of the present invention conducted the clinical study and thereby found for the first time that those peptides as shown above have a property to be presented on an antigen-presenting cell to induce CTLs in vivo in an HLA-A24 antigen-restricted manner. Such a property may be examined by determining the blood level of a tumor marker elevated in cancer patients at a defined time after the administration of the peptide, or by counting the CTL number via an HLA tetramer method (*Int. J. Cancer* 100, 565-570 (2002)).

The peptides described above may be prepared according to a method usually used in peptide chemistry. Examples of such preparations are those as described in the literatures including "Peptide Synthesis", Interscience, New York, 1966; "The Proteins", vol. 2, Academic Press Inc., New York, 1976; "Pepuchido-Gosei", Maruzen Co. Ltd., 1975; "Pepuchido-Gosei-no-Kiso-to-Jikkenn", Maruzen Co. Ltd., 1985; and "Iyakuhin-no-Kaihatu, Zoku, vol. 14, Peputido-Gosei", Hirokawa Shoten, 1991.

The peptides may have an amino acid sequence of SEQ ID NO: 2 or SEQ ID NO: 3 wherein an amino group of the N-terminal amino acid or a carboxyl group of the C-terminal amino acid is modified.

Specifically, modifying groups of the amino group of the N-terminal amino acid include an alkyl group having 1 to 6 carbon atoms, a phenyl group, a cycloalkyl group, an acyl group, and the like, of which the 1 to 3 may be selected. Examples of the acyl group include an alkanoyl group having 1 to 6 carbon atoms, an alkanoyl group having 1 to 6 carbon atoms substituted with a phenyl group, a carbonyl group substituted with a cycloalkyl group having 5 to 7 carbon atoms, a alkylsulfonyl group having 1 to 6 carbon atoms, a phenylsulfonyl group, an alkoxycarbonyl group having 2 to 6 carbon atoms, an alkoxycarbonyl group substituted with a phenyl group, a carbonyl group substituted with a cycloalkoxy having 5 to 7 carbon atoms, a phenoxycarbonyl group, and the like.

Peptides wherein a carboxyl group of the C-terminal amino acid is modified include esters and amides. Specific examples of the esters include a C1-C6 alkyl ester, a C0-C6 alkyl ester substituted with a phenyl group, a C5-C7 cycloalkyl ester, and the like, whereas specific examples of the amides include an amide, an amide substituted with one or two C1-C6 alkyl groups, an amide substituted with one or two C0-C6 alkyl groups substituted with a phenyl group, an amide that forms a 5 to 7-numbered azacycloalkane that contains the nitrogen atom of the amide, and the like.

(2) Water-in-Oil Emulsions

As used herein, a water-in-oil emulsion is referred to as an emulsion that comprises oil as an dispersion medium, and water as an dispersed liquid in which the water is dispersed as fine droplets in the oil.

An emulsifier and an oil are usually to prepare water-in-oil emulsions of the present invention. Emulsifying agents are not limited to a particular one as long as the agents allow an effective ingredient dispersed in an oil, and specifically include polyoxyethylene sorbitan mono-laurate (Polysorbate20), polyoxyethylene sorbitan mono-palmitate (Polysorbate40), and polyoxyethylene sorbitan mono-stearate (Polysorbate60). Oils usable herein include Drakeol 6VR, squalane, and ethyl oleate.

Montanide ISA (registered trademark) 720, Montanide ISA (registered trademark) 51, and the like can be appropriately used in the invention because they contain both emulsifier and oil in an adequate amount each.

The water-in-oil emulsions of the present invention may be prepared with reference to, for example, Ikuo Suzuki, et al., "Iyakuhin-no-Kaihatu, vol. 15, Seizai-no-Butsurika-gakuteki-Seishitsu", Hirokawa Shoten, 1989, October, pp 291-306. For example, a peptide as an effective ingredient is first dissolved or suspended in a distilled water or physiological saline to provide a preparation comprising an active ingredient. Then, the preparation is mixed with an emulsifier and an oil as discussed above. The mixing may be conducted with a mixer, a homogenizer, an ultrasonication homomixer, or the like. The mixing may be conducted in a hospital or a clinic.

Mixing ratio of an effective ingredient to an emulsifier and an oil may be adjusted by a person skilled in the art to be in a range that water-in-oil emulsions can be prepared. Typical ratios include Montanide ISA (registered trademark) 51:effective ingredient=50:50 (w:w), and Montanide ISA (registered trademark) 720:effective ingredient=70:30 (w:w).

The water-in-oil emulsions of the present invention may comprise either one or both of the peptides described above.

The water-in-oil emulsions of the present invention may be a formulation that is in a dosage unit form that comprises 0.1 to 100 mg, preferably 0.1 to 20 mg of the peptide. Dose of the peptide is defined as an amount necessary to induce CTLs in vivo in an HLA-A24 antigen-restricted manner, and more preferred dose is 1 to 10 mg. Particular dose may be adjusted as appropriate within the rage described above depending on the disease to be treated, the age and the weight of the patient, and the like.

The water-in-oil emulsions of the present invention may be appropriately used as a cancer vaccine. The cancer vaccine is efficient in treatment or prevention of cancers. Diseases to be administered with the cancer vaccine according to the present invention include cancers wherein the expression level of the WT1 gene is elevated, including blood cancers such as leukemia, myelodysplastic syndrome, multiple myeloma and malignant lymphoma, and solid cancers such as gastric cancer, colon cancer, lung cancer, breast cancer, embryonal cancer, hepatic cancer, skin cancer, bladder cancer, prostate cancer, uterine cancer, cervical cancer, and ovarian cancer.

In this connection, as another embodiment, the invention provides a method for treatment or prevention of a cancer, which comprises administering the water-in-oil emulsion according to the invention to a patient in need who is positive for an HLA-A24, and positive for WT1.

Administration of the emulsions of the invention may be conducted by, for example, intradermal, subcutaneous, intramuscular or intravenous injection, and intradermal and subcutaneous injections are preferred since their administrations can efficiently induce CTLs. Although the number and the interval of the administration thereof may be adjusted appropriately depending on the disease to be treated or prevented, individual differences of the patient, and the like, it is typical to administer the dosage unite form of the present invention more than once, preferably once every several days to every several months.

(3) Kits

As another embodiment, the present invention provides a kit for preparation of the water-in-oil emulsions according to the invention, which include a container comprising either one or both of peptides selected from the group consisting of a peptide having an amino acid sequence of SEQ ID NO: 2, and a peptide having an amino acid sequence of SEQ ID NO: 3, and a container comprising an emulsifier and an oil.

Containers as used in the present kit include glass or plastic vials that are allowed to be sealed. The peptide, the emulsifier and the oil are as described above.

The peptides included in a container are usually in a form of lyophilized product. In this case, the kit of the present invention also may include a container comprising a sterilized water or physiological saline in an amount to prepare a solution or suspension containing a suitable concentration of the peptide. Alternatively, the kit may include a container comprising a peptide in a state of aqueous solution or suspension.

Each of the peptide, and the emulsifier and the oil is usually comprised in a container in an amount to be administered once. For example, 0.1 to 100 mg, preferably 1 to 20 mg of the peptide is comprised in one container, whereas an amount of the emulsifier and the oil required to convert the peptide used into a water-in-oil emulsion is comprised in one container.

The kit of the present invention can be used to prepare readily the water-in-oil emulsion according to the invention just before use in a hospital or a clinic.

EXAMPLES

The present invention is further illustrated by the following examples and formulation examples, but is not limited by these examples in any respect. The clinical study in the examples was conducted on patients who had given informed consent with the approval of the Ethical Review Board of the Faculty of Medicine, Osaka University.

Example 1

Effect of Wild Type WT1 Peptide (SEQ ID NO: 2) on the Lung Cancer Patient (1)

The present example illustrates the case of the lung cancer patient (female) with metastasis at stage IV, who was administered with the WT1 peptide vaccine. The WT1 peptide used in this example was wild type WT1 peptide: Cys Met Thr Trp Asn Gln Met Asn Leu (SEQ ID NO: 2) synthesized by MPS Inc. (U.S.) with GMP grade, which was a partial peptide from positions 235 to 243 of the WT1 protein being demonstrated to be presented on the HLA-A* 2402 molecule so as to induce peptide-specific CTLs.

A solution of the wild type WT1 peptide is mixed with the same weight of MONTANIDE ISA (registered trademark) 51 (SEPPIC, Inc.), an adjuvant comprising mineral oil and the surfactant mannite oleate, to provide a water-in-oil emulsion. Eight hundreds µl of 1 mg/ml peptide solution was poured into 800 mg (about 1016 µl) of MONTANIDE ISA (registered trademark) 51, and a glass syringe attached with a 21G needle was used to take in and out the mixture 10 times in a beaker in order to complete the mixing, thereby providing an emulsion.

As such, 680 µl aliquot of the emulsion (0.3 mg of the peptide) was prepared each just before the administration. For the administration, the emulsion aliquot was injected intradermally at the upper arm of the patient totally seven times, i.d. on day 0, 14, 28, 42, 56, 85, and 99 wherein day 0 represents the day when the first administration was conducted. The blood level of a tumor marker, CEA, in the patient was about 400 ng/ml nine months before the peptide administration, and the level increased drastically, reaching about 2000 ng/ml two months before the peptide administration.

The change in the tumor marker levels beginning on the day before the peptide administration is shown in FIG. 1. CEA (carcinoembryonic antigen) was determined using IMxCEA Dinapack (Dinabbott, Inc.), whereas SLX (sialyl Lex-i antigen) was determined by Sumikin Bio-Science Co., Ltd.

FIG. 1 shows that the increase in the level of CEA in blood was suppressed by the administration of the peptide, and especially the blood level was significantly decreased on and after the 5th administration. FIG. 1 also shows that the level of SLX in blood was increased until the 4th administration of the peptide, but subsequently, the increase was suppressed so that the blood level was stabilized at the lower one.

Typical delayed type hypersensitivity (DTH) was determined to check the immune response specific for the peptide administrated. It was found that the 5th administration induced a strong swelling at the site of the peptide administration, suggesting that a specific immunity was established.

Further, the establishment of a specific immunity was also suggested by ELISPOT method (*J. Immunol. Meth*, 110: 29, 1988) whereby T cells producing IFN-γ in response to specifically the peptide were found to be more in the peripheral blood mononuclear cells (PBMC) receiving the peptide in comparison with the PBMC not receiving the peptide.

Those results show that the administration of the water-in-oil emulsion comprising the wild type WT1 peptide (SEQ ID NO: 2) suppressed the development of the tumor.

Example 2

Effect of Wild Type WT1 Peptide (SEQ ID NO: 2) on the Lung Cancer Patient (2)

The present example illustrates the case of the lung cancer patient (male) with metastasis at stage IV, who was administered with the WT1 peptide vaccine. In a similar manner to Example 1, a solution of wild type WT1 peptide (SEQ ID NO: 2) was mixed with Montanide ISA (registered trademark) 51 to provide a water-in-oil emulsion each just before the administration wherein the emulsion was injected intradermally at the upper arm of the patient totally six times, i.d. on day 0, 14, 28, 42, 56, and 71 wherein day 0 represents the day when the first administration was conducted.

Figure 2:
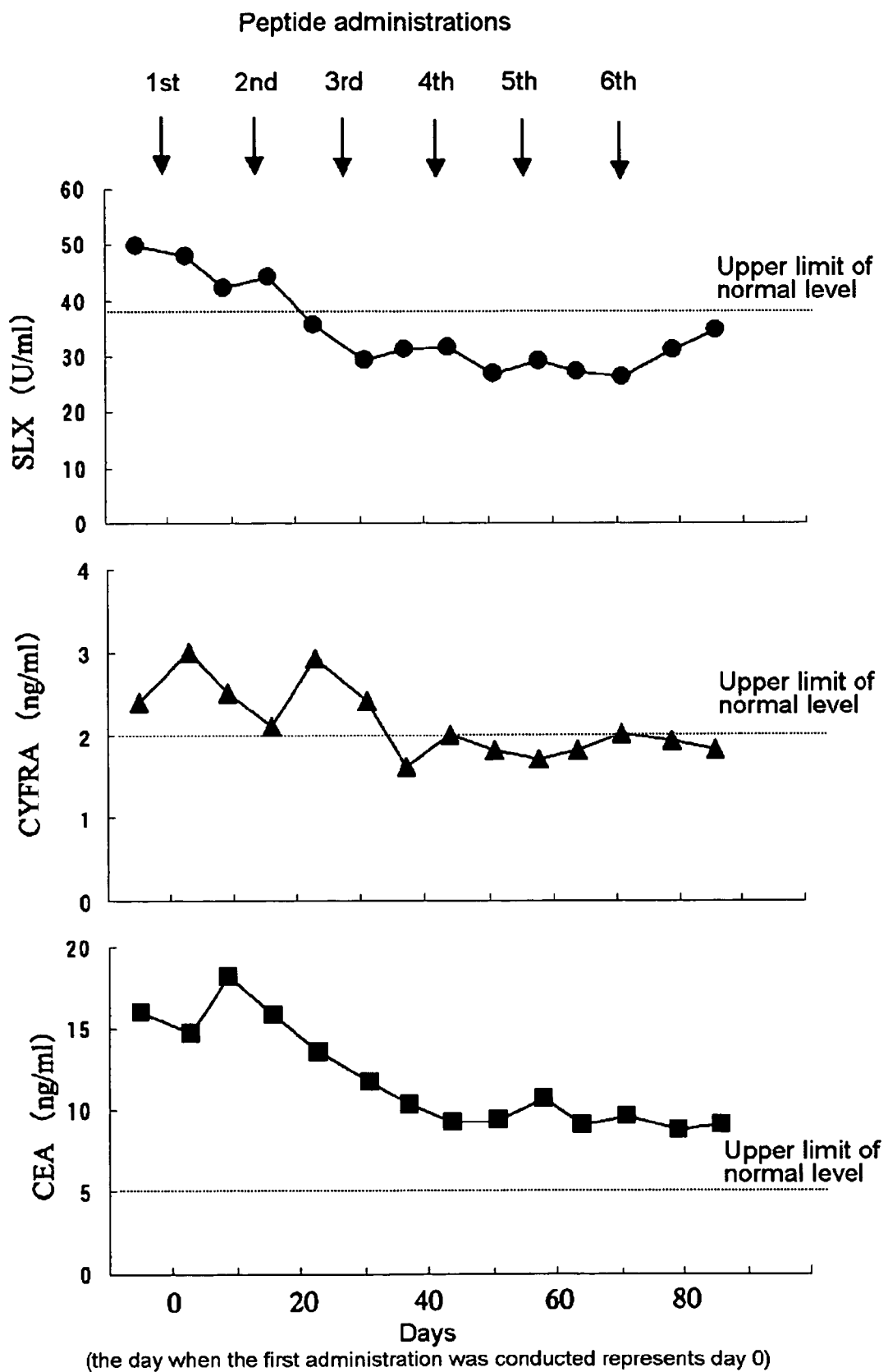
FIG. 2 is graphs showing the change in tumor marker levels in the lung cancer patient (male) before and after the administration of wild type WT1 peptide (SEQ ID NO: 2).

The change in the tumor marker levels before and after the peptide administration is shown in FIG. 2. The levels of tumor markers, CEA and SLX, were determined in a similar manner to Example 1, and the level of CYFRA (cytokeratin 19 fragments) was determined using Elecsys CYFRA produced by Roche.

FIG. 2 shows that the level of SLX in blood before the peptide administration was 50 U/ml, which is higher than the upper limit of normal level, 38 U/ml, and the level was decreased to reach the normal level on and after the 2nd administration. FIG. 2 also shows that the level of CYFRA in blood before the peptide administration was higher than the upper limit of normal level, 2 ng/ml, and the level was decreased to below the upper limit of normal level on and after the 3rd administration. Additionally, FIG. 2 shows that the level of CEA in blood before the peptide administration, which was higher than the upper limit of normal level, 5 ng/ml, was decreased on and after the 2nd administration.

Those results show that the administration of the water-in-oil emulsion comprising the wild type WT1 peptide (SEQ ID NO: 2) suppressed the development of the tumor.

Example 3

Effect of Altered Type WT1 Peptide (SEQ ID NO: 3) on the Leukemia Patient

The present example illustrates the case of the cancer patient (male) suffered from acute myeloblastic leukemia (AML-M1) transformed from Myelodysplastic Syndromes (MDS), who was administered with the WT1 peptide vaccine. The WT1 peptide used in this example was altered type WT1 peptide: Cys Tyr Thr Trp Asn Gln Met Asn Leu (SEQ ID NO: 3) synthesized by MPS Inc. (U.S.) with GMP grade. In a similar manner to Example 1, the peptide was mixed with MONTANIDE ISA (registered trademark) 51 to provide a water-in-oil emulsion, and the emulsion was injected intradermally at the upper arm of the patient. Leukemic blasts occupied 50% of the bone marrow two days before the administration, while the total number of leukocytes was 1500/μl on the day before the administration. Two days after the administration, the total number of leukocytes was decreased to 700/μl, and the leukemic blasts of the bone marrow reduced to 27%. When a hemopoietic factor, G-CSF, was administered to the patient in the light of the decreased total number of leukocytes, the total number recovered to 2150/μl, and the leukemic blasts of the bone marrow was 11% seven days after the administration.

Those results show that the administration of the water-in-oil emulsion comprising the altered type WT1 peptide (SEQ ID NO: 3) improved the conditions of leukemia with decreased ratio of the leukemic blasts in the bone marrow.

Subsequently, the number of cytotoxic T cells (CTLs) reactive to the wild type WT1 peptide-presenting HLA-A*2402 molecule in the same patient was determined by an HLA tetramer method. The HLA-A*2402 tetramer was prepared using the wild type WT1 peptide according to the method described in *Int. J. Cancer* 100, 565-570 (2002). On a flow cytometer, FACS, the cells were stained with the two colors of PE-labeled HLA-A*2402 tetramer and FITC-labeled CD8 antibody, and the double-positive cells were assigned to CTLs recognizing the wild type WT1 peptide, i.e., CTLs reactive to WT1-positive cancer cells. CTL frequency three days before the administration of the peptide was 1.1%, whereas the frequency was increased to 8.8% two days after the administration.

This result shows that the administration of the water-in-oil emulsion comprising the WT1 peptide allowed to dramatically increase the CTLs reactive to WT1-positive cancer cells. This also suggests that the CTLs may destroy the leukemic blasts to reduce the leukemic blasts ratio in the bone marrow.

INDUSTRIAL APPLICABILITY

The present invention provides water-in-oil emulsions which comprise as an effective ingredient an HLA-A24-restricted peptide derived from WT1 which has an activity to induce CTLs in clinical study, and kits for preparation of the same. The invention would be efficient to improve the conditions of many cancer patients.

SEQUENCE LISTING

```
<160> NUMBER OF SEQ ID NOS: 3

<210> SEQ ID NO 1
<211> LENGTH: 449
<212> TYPE: PRT
<213> ORGANISM: Homo sapiens

<400> SEQUENCE: 1

Met Gly Ser Asp Val Arg Asp Leu Asn Ala Leu Leu Pro Ala Val Pro
 1               5                   10                  15
```

-continued

```
Ser Leu Gly Gly Gly Gly Cys Ala Leu Pro Val Ser Gly Ala Ala
         20                  25                  30

Gln Trp Ala Pro Val Leu Asp Phe Ala Pro Pro Gly Ala Ser Ala Tyr
         35                  40                  45

Gly Ser Leu Gly Gly Pro Ala Pro Pro Ala Pro Pro Pro Pro
 50                  55                  60

Pro Pro Pro Pro His Ser Phe Ile Lys Gln Glu Pro Ser Trp Gly Gly
 65                  70                  75                  80

Ala Glu Pro His Glu Glu Gln Cys Leu Ser Ala Phe Thr Val His Phe
                 85                  90                  95

Ser Gly Gln Phe Thr Gly Thr Ala Gly Ala Cys Arg Tyr Gly Pro Phe
                100                 105                 110

Gly Pro Pro Pro Ser Gln Ala Ser Ser Gly Gln Ala Arg Met Phe
             115                 120                 125

Pro Asn Ala Pro Tyr Leu Pro Ser Cys Leu Glu Ser Gln Pro Ala Ile
130                 135                 140

Arg Asn Gln Gly Tyr Ser Thr Val Thr Phe Asp Gly Thr Pro Ser Tyr
145                 150                 155                 160

Gly His Thr Pro Ser His His Ala Ala Gln Phe Pro Asn His Ser Phe
                165                 170                 175

Lys His Glu Asp Pro Met Gly Gln Gln Gly Ser Leu Gly Glu Gln Gln
                180                 185                 190

Tyr Ser Val Pro Pro Pro Val Tyr Gly Cys His Thr Pro Thr Asp Ser
             195                 200                 205

Cys Thr Gly Ser Gln Ala Leu Leu Leu Arg Thr Pro Tyr Ser Ser Asp
210                 215                 220

Asn Leu Tyr Gln Met Thr Ser Gln Leu Glu Cys Met Thr Trp Asn Gln
225                 230                 235                 240

Met Asn Leu Gly Ala Thr Leu Lys Gly Val Ala Ala Gly Ser Ser Ser
                245                 250                 255

Ser Val Lys Trp Thr Glu Gly Gln Ser Asn His Ser Thr Gly Tyr Glu
                260                 265                 270

Ser Asp Asn His Thr Thr Pro Ile Leu Cys Gly Ala Gln Tyr Arg Ile
             275                 280                 285

His Thr His Gly Val Phe Arg Gly Ile Gln Asp Val Arg Arg Val Pro
             290                 295                 300

Gly Val Ala Pro Thr Leu Val Arg Ser Ala Ser Glu Thr Ser Glu Lys
305                 310                 315                 320

Arg Pro Phe Met Cys Ala Tyr Pro Gly Cys Asn Lys Arg Tyr Phe Lys
                325                 330                 335

Leu Ser His Leu Gln Met His Ser Arg Lys His Thr Gly Glu Lys Pro
                340                 345                 350

Tyr Gln Cys Asp Phe Lys Asp Cys Glu Arg Arg Phe Ser Arg Ser Asp
             355                 360                 365

Gln Leu Lys Arg His Gln Arg Arg His Thr Gly Val Lys Pro Phe Gln
370                 375                 380

Cys Lys Thr Cys Gln Arg Lys Phe Ser Arg Ser Asp His Leu Lys Thr
385                 390                 395                 400

His Thr Arg Thr His Thr Gly Lys Thr Ser Glu Lys Pro Phe Ser Cys
                405                 410                 415

Arg Trp Pro Ser Cys Gln Lys Lys Phe Ala Arg Ser Asp Glu Leu Val
                420                 425                 430
```

```
Arg His His Asn Met His Gln Arg Asn Met Thr Lys Leu Gln Leu Ala
        435                 440                 445
Leu

<210> SEQ ID NO 2
<211> LENGTH: 9
<212> TYPE: PRT
<213> ORGANISM: Artificial Sequence
<220> FEATURE:
<223> OTHER INFORMATION: Synthetic peptide derived from positions 235 to
      243 of human WT1

<400> SEQUENCE: 2

Cys Met Thr Trp Asn Gln Met Asn Leu
  1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic peptide of human WT1 wherein Met at
      position 236 in the spanning region of positions 235 to 243 is
      altered into Tyr

<400> SEQUENCE: 3

Cys Tyr Thr Trp Asn Gln Met Asn Leu
  1               5
```

The invention claimed is:

1. A water-in-oil emulsion which comprises as an effective ingredient a peptide having the amino acid sequence of Cys Tyr Thr Trp Asn Gln Met Asn Leu (SEQ ID NO: 3).

2. The emulsion according to claim 1, wherein the emulsion is in a dosage unit form that comprises 0.1 to 100 mg of the peptide.

3. The emulsion according to claim 1 or 2, wherein the emulsion is to be used as a cancer vaccine.

4. A process for preparation of the water-in-oil emulsion according to claim 1, which comprises mixing a preparation comprising a peptide having an amino acid sequence of Cys Tyr Thr Trp Asn Gln Met Asn Leu (SEQ ID NO: 3), together with an emulsifier and an oil.

5. A kit for preparation of the water-in-oil emulsion according to claim 1, which includes a container comprising a peptide having the amino acid sequence of Cys Tyr Thr Trp Asn Gln Met Asn Leu (SEQ ID NO: 3), and a container comprising an emulsifier and an oil.

6. The kit according to claim 5, wherein the kit is to be used to prepare the water-in-oil emulsion according to claim 1 just before use.

7. A method for treatment of acute myeloblastic leukemia (AML-M1) in a patient in need thereof who is positive for an HLA-A24 and positive for WT1, which comprises administering a water-in-oil emulsion which comprises as an effective ingredient a peptide having the amino acid sequence of Cys Tyr Thr Trp Asn Gln Met Asn Leu (SEQ ID NO: 3).

* * * * *